United States Patent [19]

Ito et al.

[11] Patent Number: 5,264,450
[45] Date of Patent: Nov. 23, 1993

[54] IMIDAZOLE SUBSTITUTED CYCLOALKANOL DERIVATIVES AND FUNGICIDAL COMPOSITIONS CONTAINING SAME

[75] Inventors: Atsushi Ito; Toshihide Saishoji; Satoru Kumazawa, all of Iwaki, Japan

[73] Assignee: Kureha Kagaku Kogyo Kabushiki Kaisha, Tokyo, Japan

[21] Appl. No.: 863,007

[22] Filed: Apr. 6, 1992

Related U.S. Application Data

[62] Division of Ser. No. 550,836, Jul. 10, 1990, Pat. No. 5,124,345.

[30] Foreign Application Priority Data

Aug. 15, 1989 [JP] Japan .................................. 1-210502

[51] Int. Cl.$^5$ .................... A01N 43/50; C07D 233/60
[52] U.S. Cl. .................................. 514/399; 548/341.1
[58] Field of Search .................... 548/341.1; 514/399

[56] References Cited

U.S. PATENT DOCUMENTS

| | | | |
|---|---|---|---|
| 4,684,396 | 8/1987 | Clough et al. .......................... 71/92 |
| 5,028,254 | 7/1991 | Kumazawa et al. ................. 514/399 |
| 5,095,028 | 3/1992 | Ito et al. ............................... 514/399 |

Primary Examiner—Patricia L. Morris
Attorney, Agent, or Firm—Nixon & Vanderhye

[57] ABSTRACT

The present invention discloses an azole-substituted cycloalkanol derivative represented by the formula (I) available for agricultural and horticultural fungicide and a process for preparing the same:

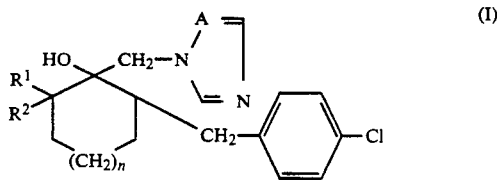

wherein $R^1$ represents a lower alkyl group, $R^2$ represents a hydrogen atom or a lower alkyl group, n is an integer of 1 or 2 and A represents a nitrogen atom or a CH group.

4 Claims, 10 Drawing Sheets

IMIDAZOLE SUBSTITUTED CYCLOALKANOL DERIVATIVES AND FUNGICIDAL COMPOSITIONS CONTAINING SAME

This application is a division of application Ser. No. 07/550,836, filed Jul. 10, 1990, now U.S. Pat. No. 5,124,345.

BACKGROUND OF THE INVENTION

This invention relates to an azole-substituted cycloalkanol derivative represented by the formula (I) which is available for an agricultural and horticultural fungicide, a process for producing the same and an agricultural and horticultural fungicide containing said derivative as an active ingredient:

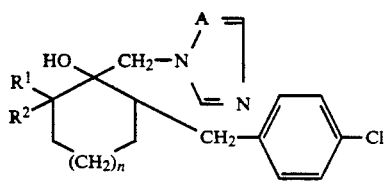
(I)

wherein $R^1$ represents a lower alkyl group, $R^2$ represents a hydrogen atom or a lower alkyl group, n is an integer of 1 or 2, and A represents a nitrogen atom or a CH group.

Heretofore, enormous research has been carried out on an azole derivative which is available for agriculture and horticulture and a large number of compounds showing specific biological activities have been found and provided for practical use. For example, Triadimefon and Propiconazole have been known as fungicides.

Among published patents, azole derivatives having a cyclohexane ring or a cycloheptane ring to which a benzyl group is bonded have been described. For example, these azole derivatives have been included in the following formula:

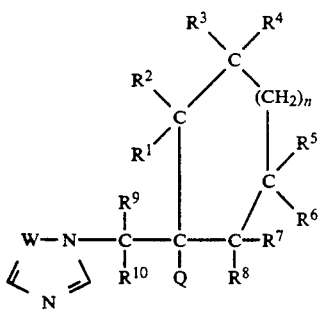

and stereoisomers thereof, wherein W is CH or N; Q is optionally substituted aryl (especially optionally substituted phenyl), optionally substituted aralkyl, or alkyl; $R^1$, $R^2$, $R^3$, $R^4$, $R^5$, $R^6$, $R^7$ and $R^8$, which may be the same or different, are H, hydroxy, alkyl, cycloalkyl, optionally substituted aralkyl, or optionally substituted phenyl, or any pair thereof may, together with the adjacent carbon atom, represent a carbonyl group (C=O); $R^9$ and $R^{10}$, which may be the same or different, are H, alkyl, cycloalkyl, optionally substituted aralkyl, or optionally substituted phenyl, and n is 0 or 1; as disclosed in U.S. Pat. No. 4,684,396 or EP-A-0 153 797.

Also, in Example 2 and Example 5 of GB Patent 2 153 355, the following compounds are exemplified:

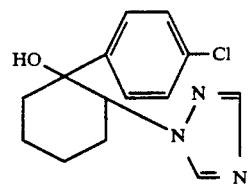

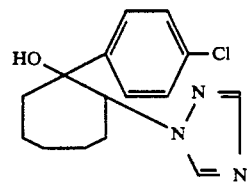

Further, in EP-A-0 324 646, the compound having the following formula has been disclosed which is different from the present compound (I) in having no lower alkyl group on the cycloalkane ring:

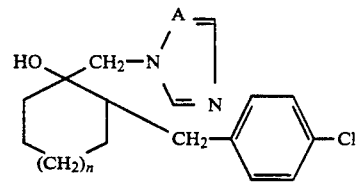

wherein n is an integer of 1 or 2 and A represents a nitrogen atom or a CH group.

The above compound is the most similar to the present compound (I) but the fact that the present compound (I) has superior effect to those of the compound disclosed in EP-A-0 324 646 is shown in Example 17 of the present specification.

The present inventors have synthesized many azole derivatives in order to develop an agricultural and horticultural fungicide which has low toxicity to human and domestic animals, high safety in handling and shows excellent fungicidal effect to various plant and crop damages, and investigated their practicability. And as the results, they have found that the azole-substituted cycloalkanol derivative represented by the above formula (I) shows the above characteristics to accomplish the present invention.

Figure 1:
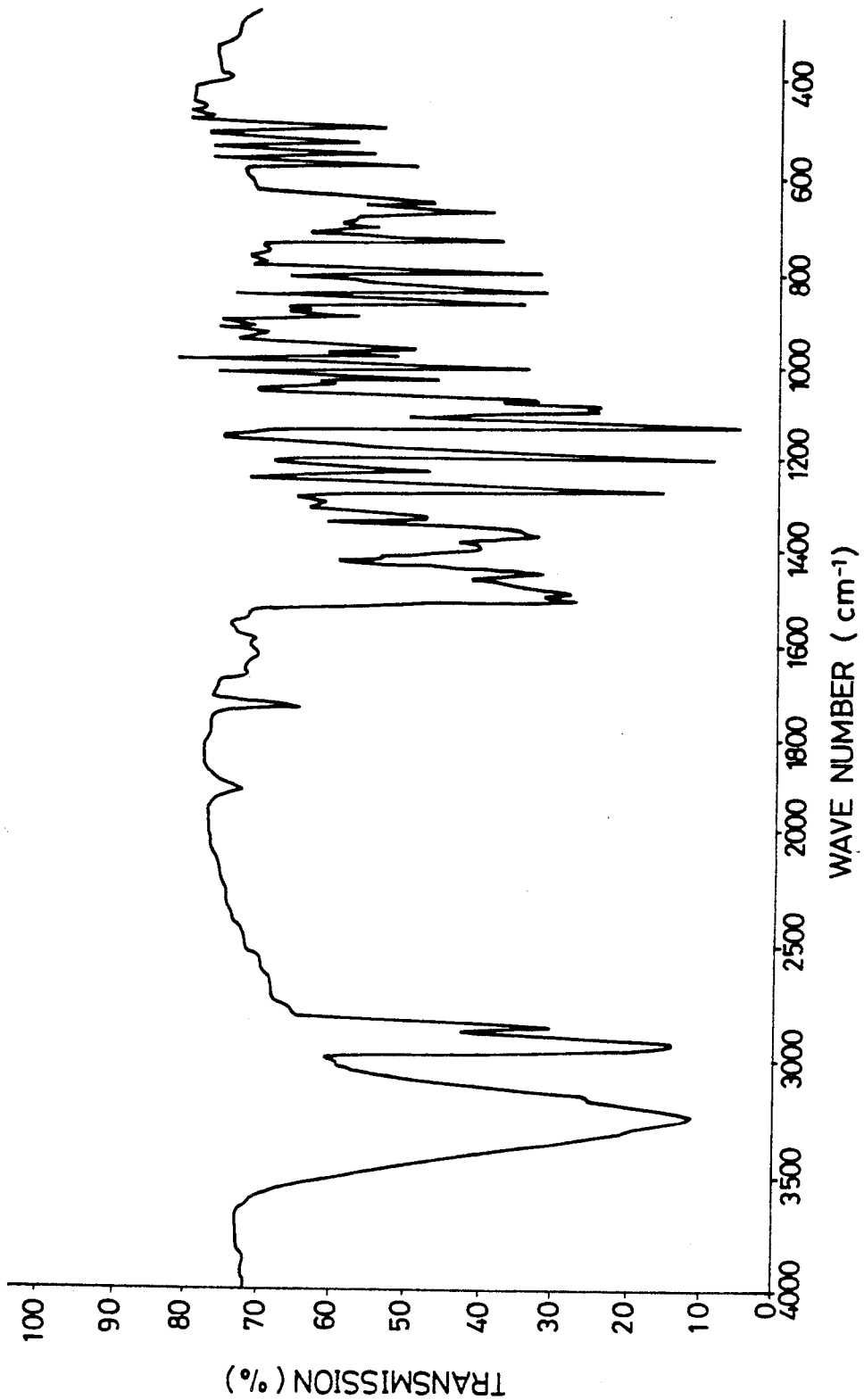
FIGS. 1 to 10 attached hereto show infrared absorption spectrum of the derivatives of the present invention shown in Table 1.
Figure 2:
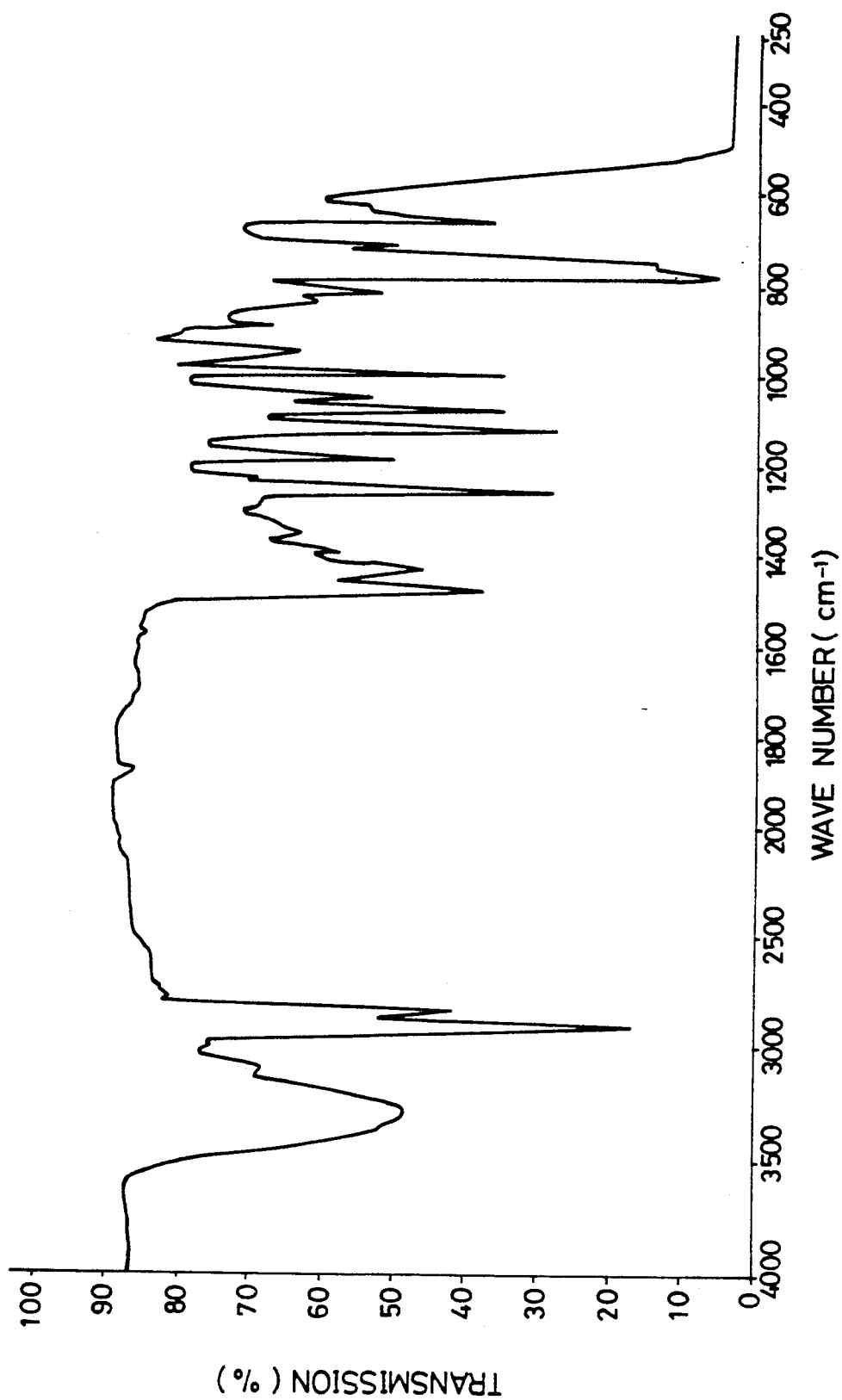
Figure 3:
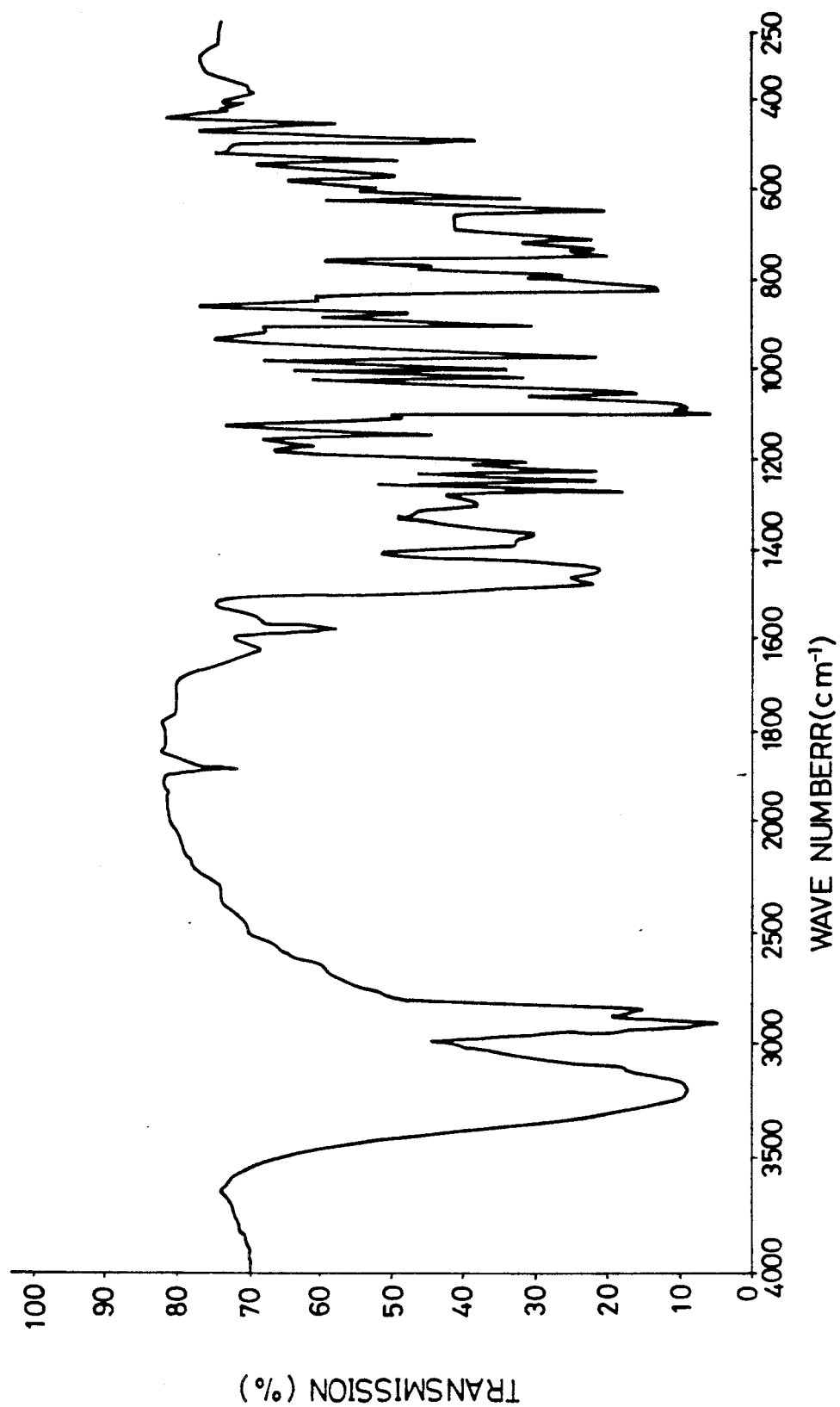
Figure 4:
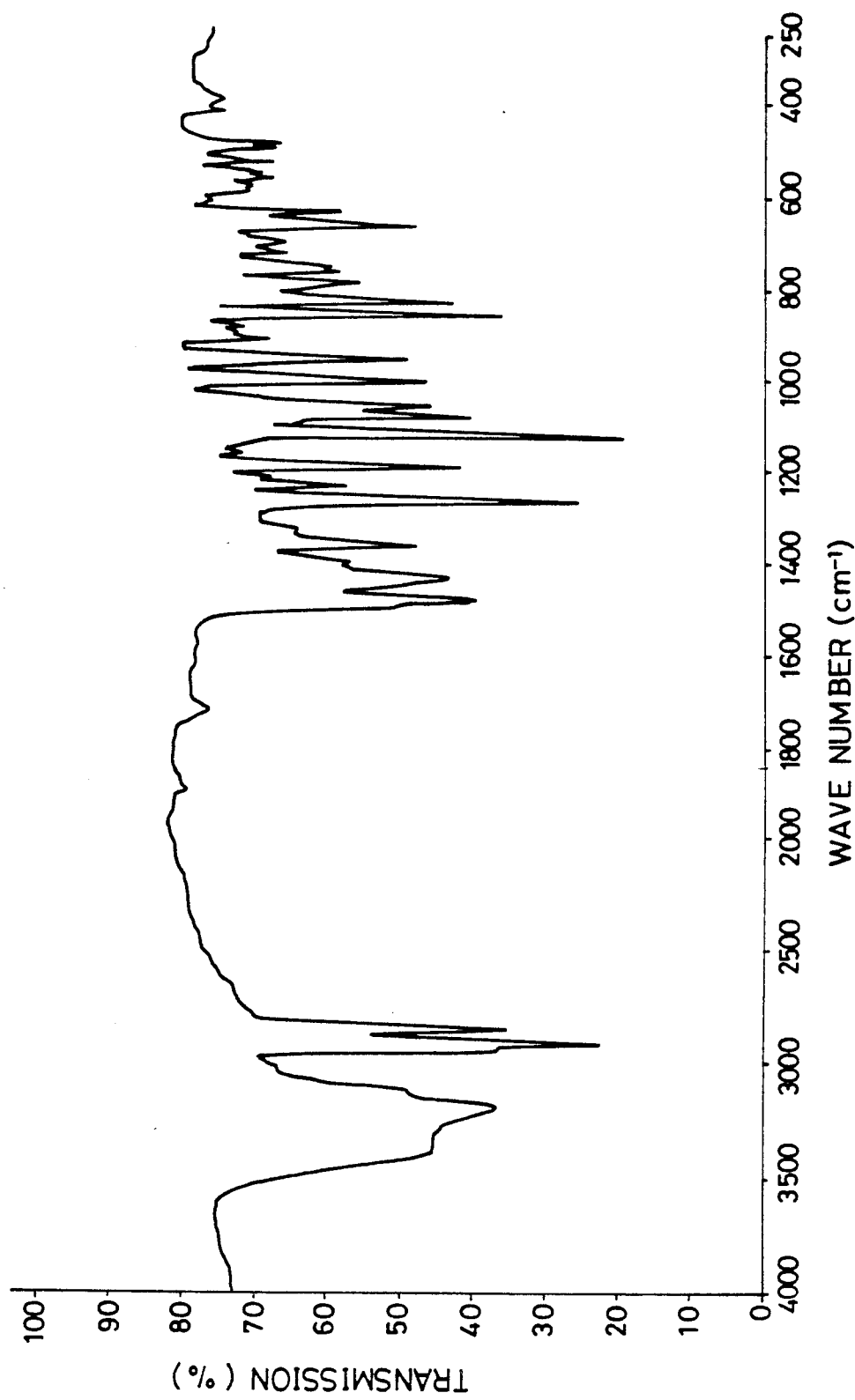
Figure 5:
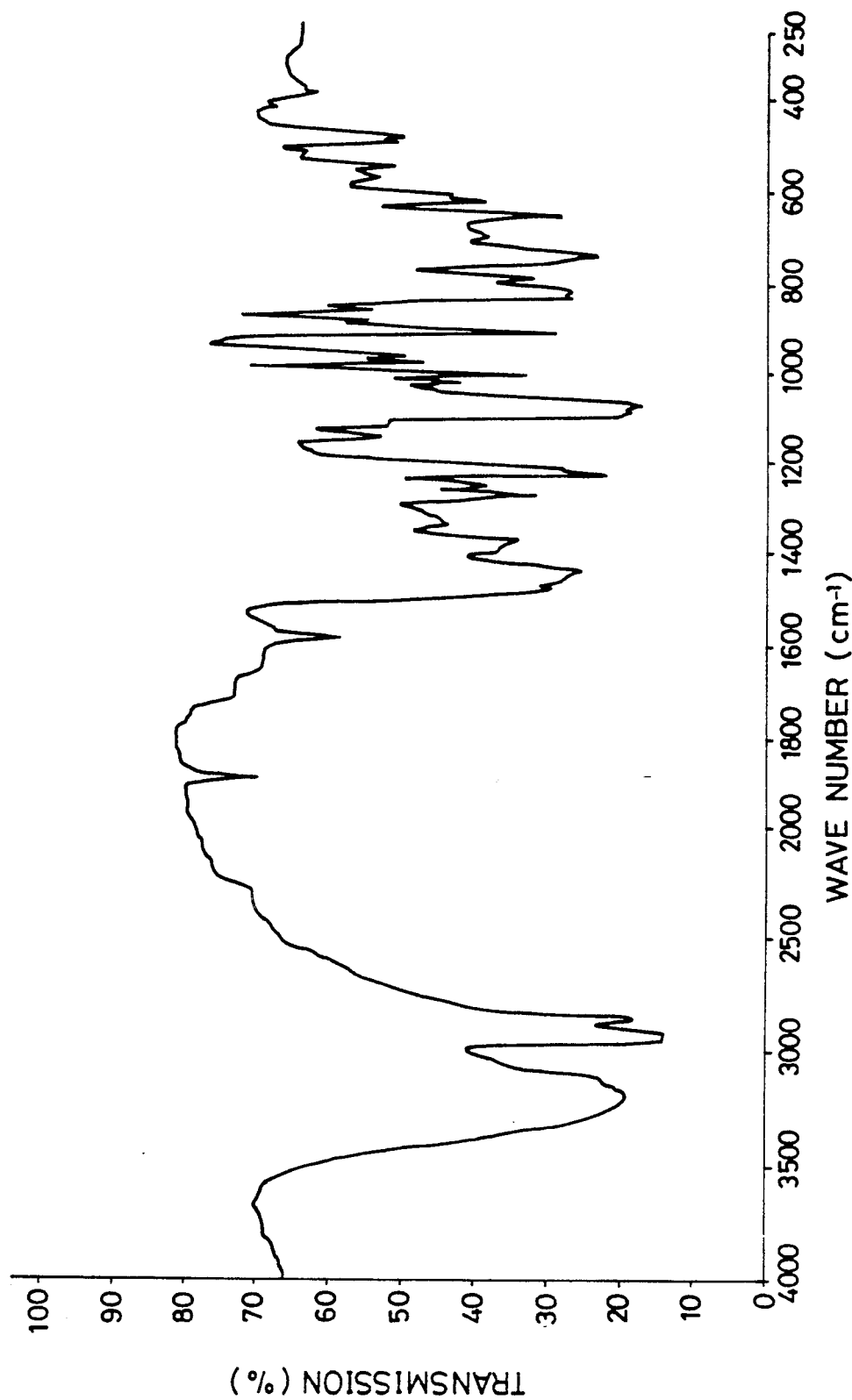
Figure 6:
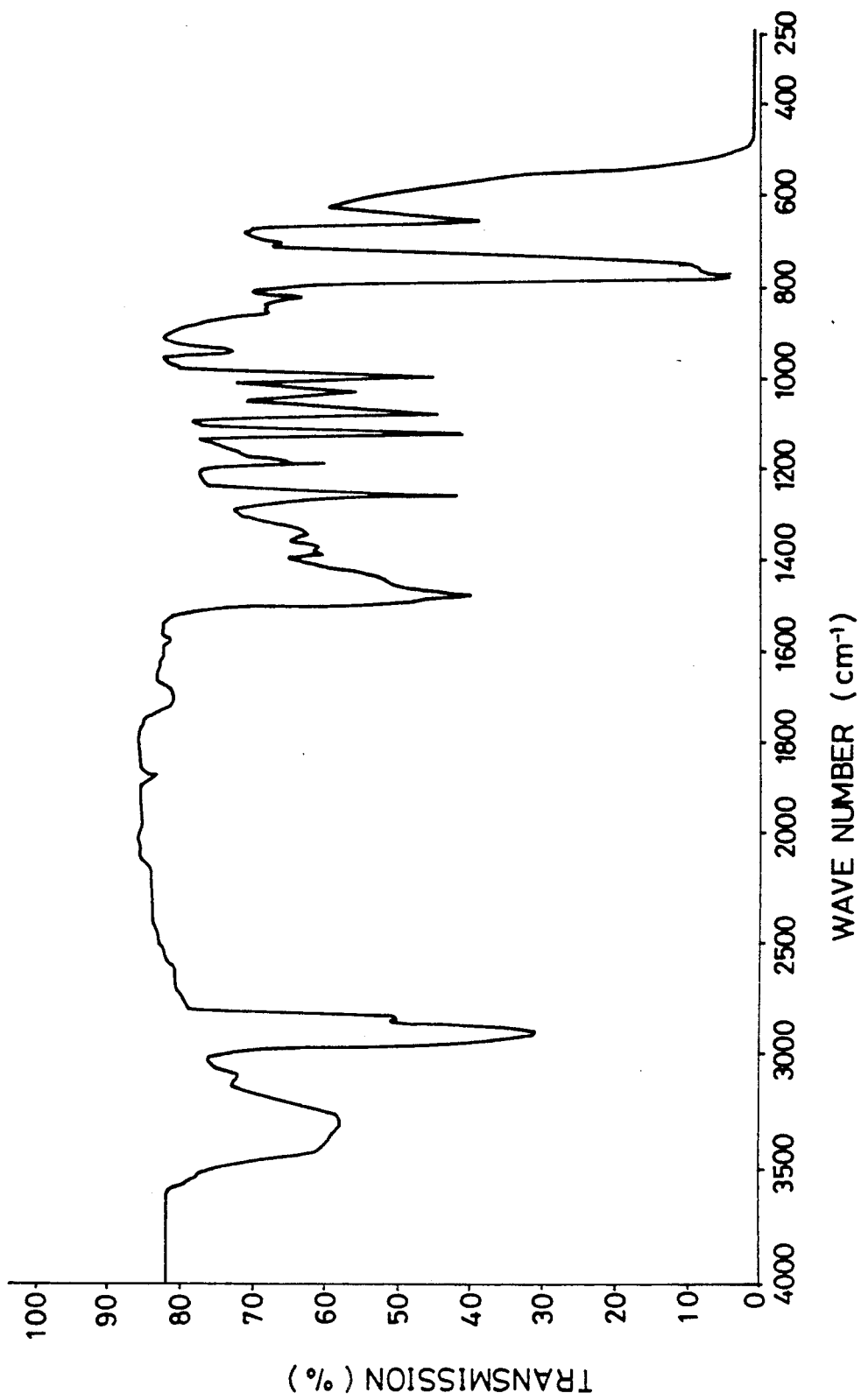
Figure 7:
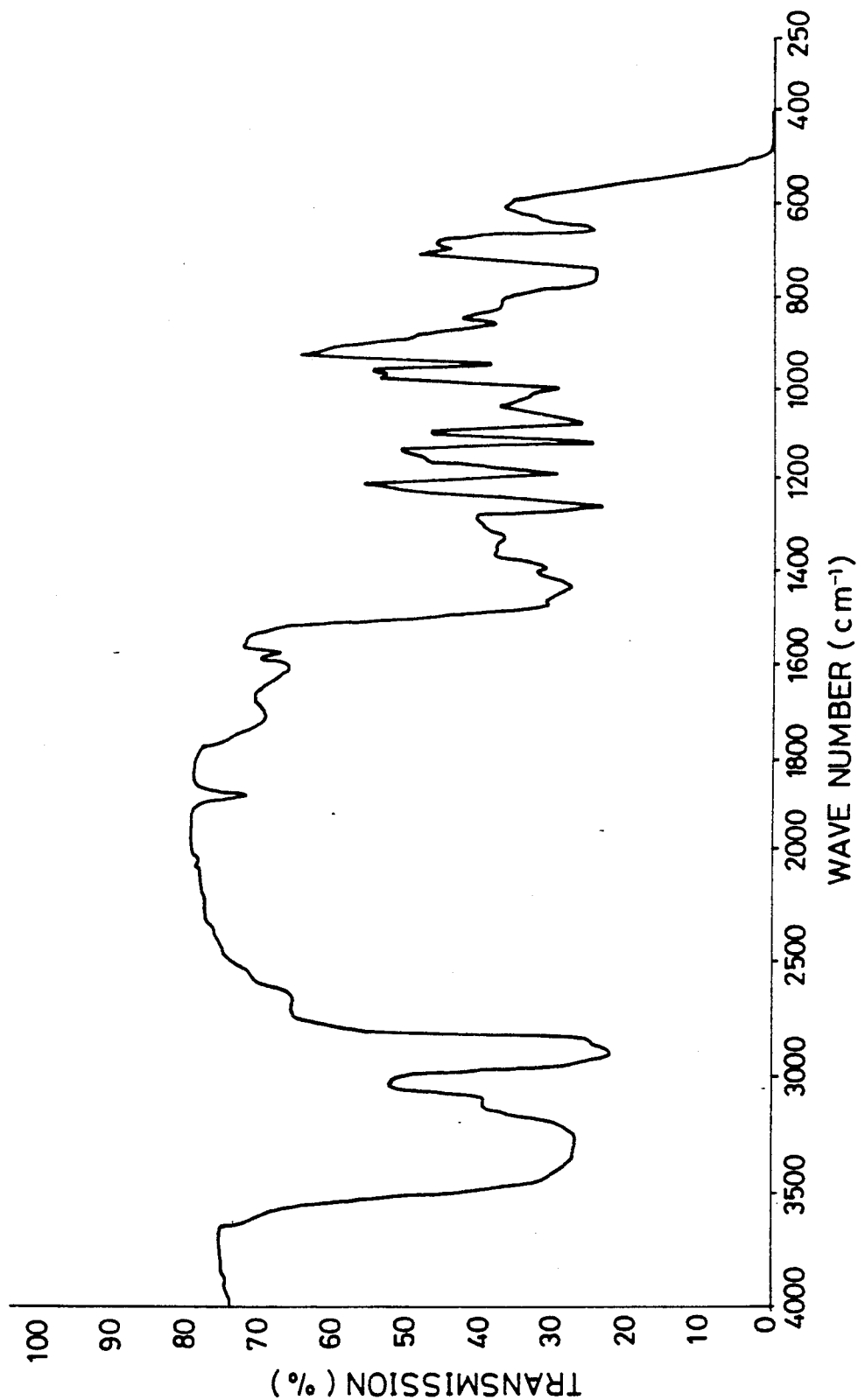
Figure 8:
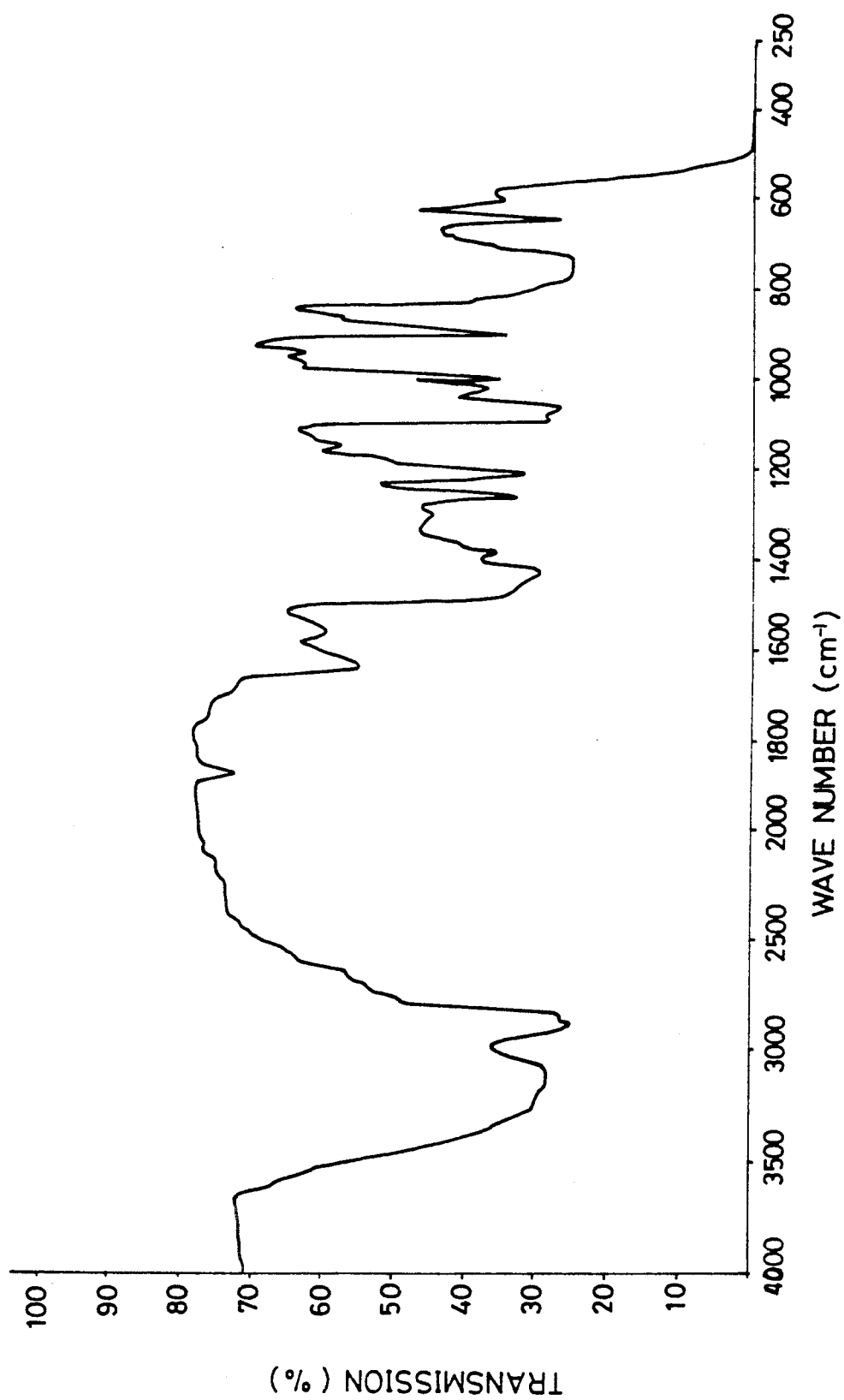
Figure 9:
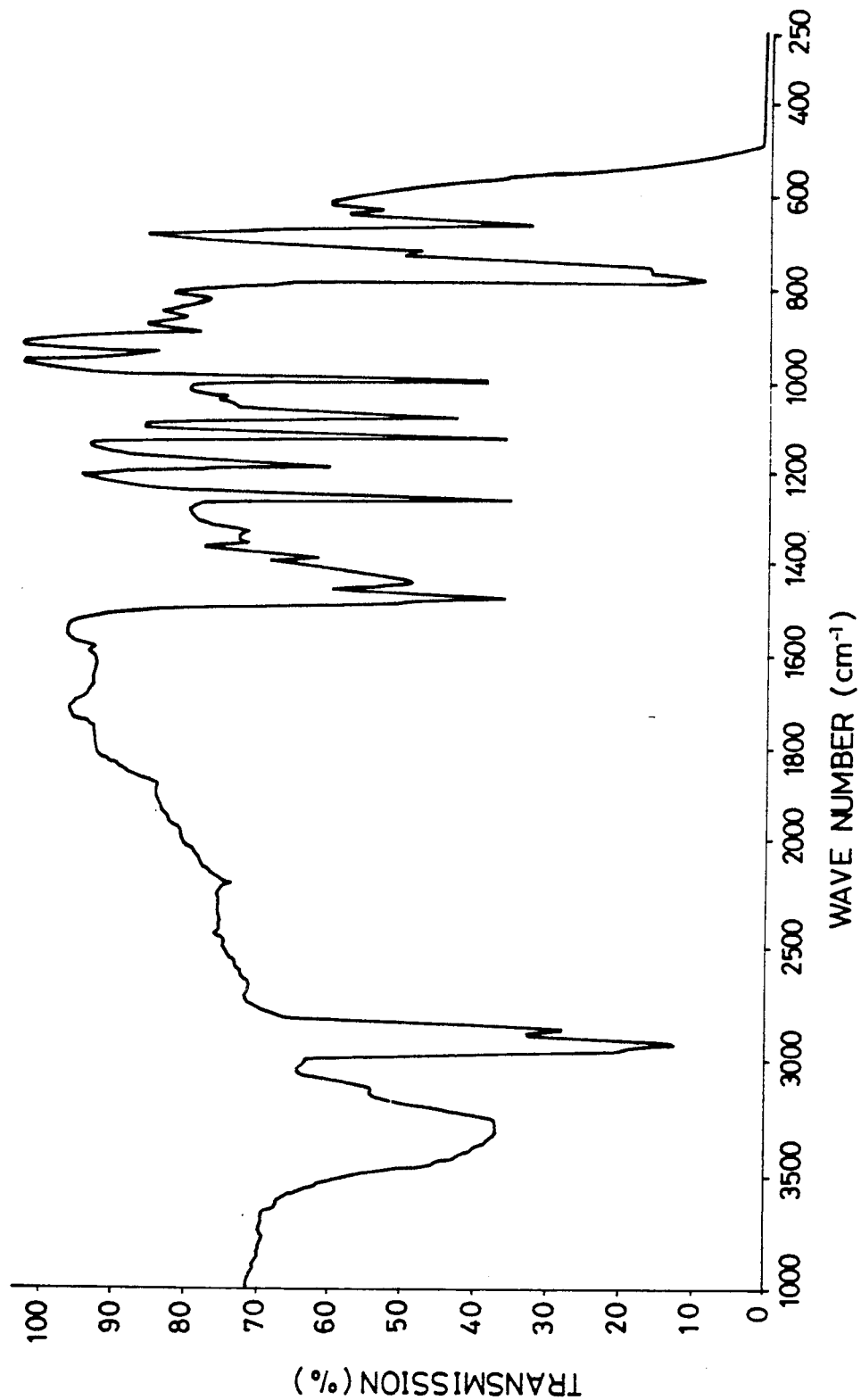
Figure 10:
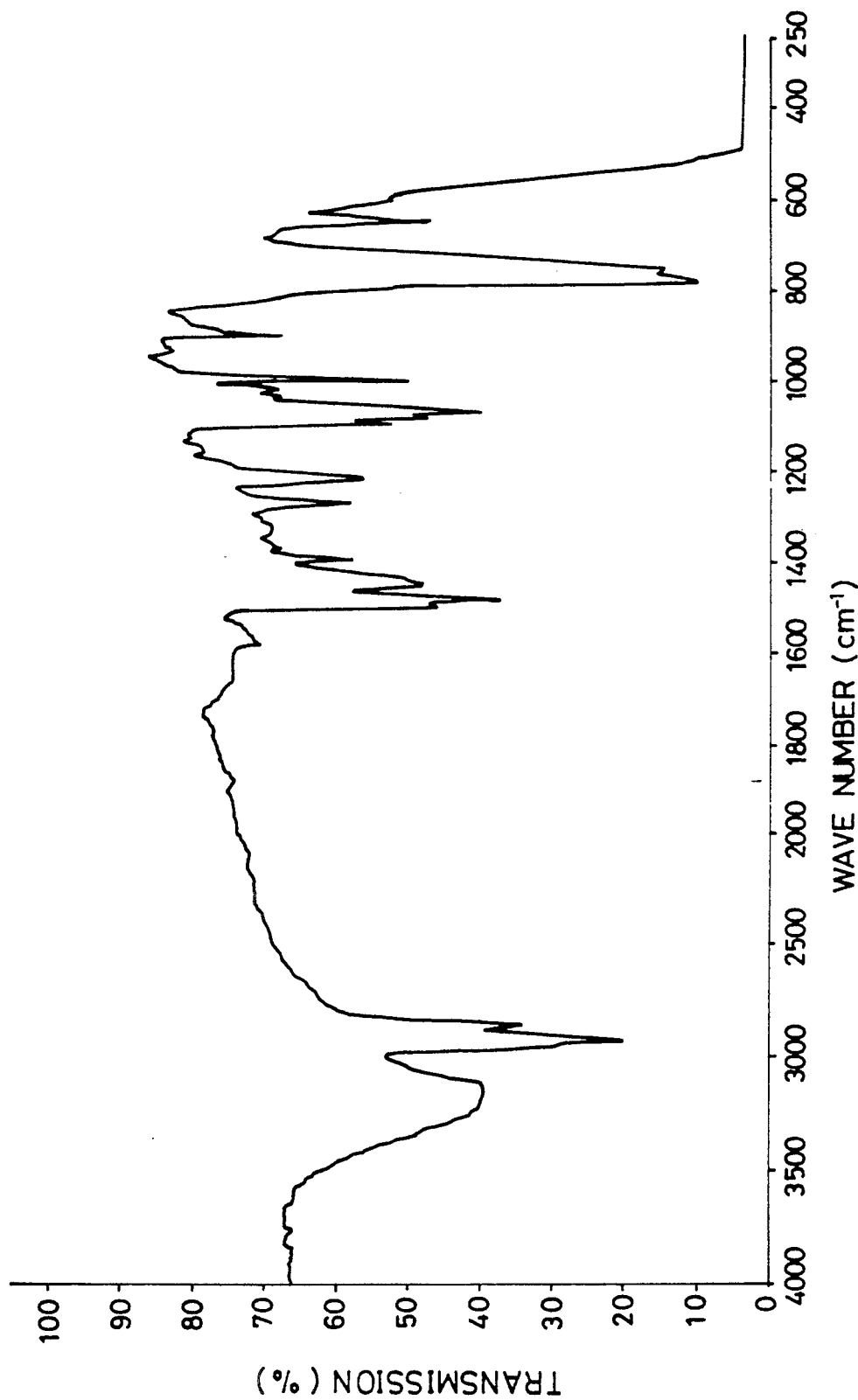

| Figure number | Compound number |
|---|---|
| 1 | I-1 |
| 2 | I-2 |
| 3 | I-3 |
| 4 | I-4 |
| 5 | I-5 |
| 6 | I-6 |
| 7 | I-7 |
| 8 | I-8 |
| 9 | I-9 |
| 10 | I-10 |

SUMMARY OF THE INVENTION

An object of the present invention is to provide an azole-substituted cycloalkanol derivative represented by the formula (I):

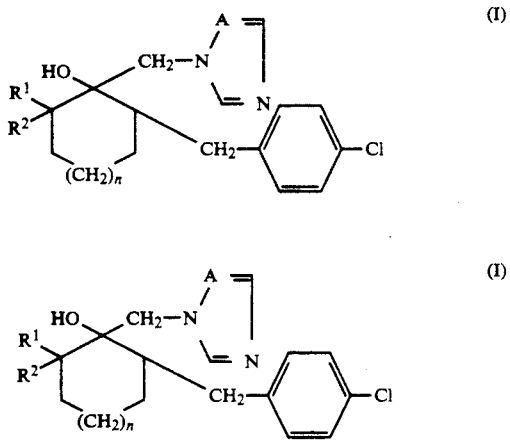

wherein $R^1$ represents a lower alkyl group, $R^2$ represents a hydrogen atom or a lower alkyl group, n is an integer of 1 or 2, and A represents a nitrogen atom or a CH group.

Another object of the present invention is to provide an agricultural and horticultural fungicide containing said cycloalkanol derivatives represented by the formula (I) as an active ingredient.

A further object of the present invention is to provide a process for preparing the cycloalkanol derivatives represented by the above formula (I).

A still further object of the present invention is to provide an oxirane derivative (II), a methylenecycloalkane derivative (IV), cycloalkane carboxylic acid ester derivatives (V) and (VII), and 3-(4-chlorobenzyl)-2-oxocycloalkane carboxylic acid alkyl ester (VIII) which are available for production of the cycloalkanol derivative represented by the formula (I).

DETAILED EXPLANATION OF THE INVENTION

The present invention relates to an azole-substituted cycloalkanol derivative represented by the formula (I):

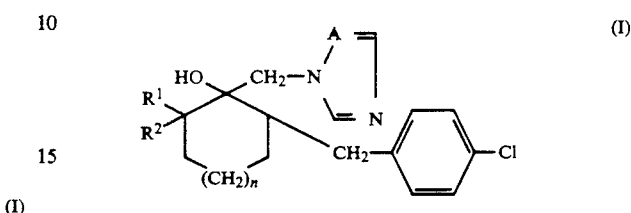

wherein $R^1$ represents a lower alkyl group, $R^2$ represents a hydrogen atom or a lower alkyl group, n is an integer of 1 or 2, and A represents a nitrogen atom or a CH group; a process for producing said cycloalkanol derivative, and oxirane derivative (II), a methylenecycloalkane derivative (VI), cycloalkane carboxylic acid ester derivatives (V) and (VII), and 3-(4-chlorobenzyl)-2-oxocycloalkane carboxylic acid alkyl ester (VIII) which are available as an intermediate for production of the same, and an agricultural and horticultural fungicide containing the above azole-substituted cycloalkanol derivative as an active ingredient.

In the present invention, "a lower alkyl group" refers to an alkyl group having 1 to 5 carbon atoms, preferably 1 to 2 carbon atoms, and exemplified by a methyl group, an ethyl group, a 1-methylethyl group, a propyl group, a 2-methylpropyl group, a butyl group, a 3-methylbutyl group, a pentyl group, and the like.

Physical and chemical properties of the above azole-substituted cycloalkanol derivative represented by the formula (I) and the above respective intermediates are as shown in Tables I to VII.

Each of these intermediates is a novel compound.

TABLE I

An Azole-substituted Cycloalkanol Derivative of the Formula (I)

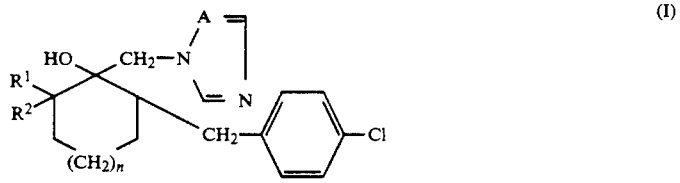

| Compound No. | Indication in Formula (I) | | | | Physical Properties (below line is m.p. in °C.) | NMR Spectrum Data (CDCl$_3$ δ ppm) |
|---|---|---|---|---|---|---|
| | $R^1$ | $R^2$ | n | A | | |
| I-1 | CH$_3$ | CH$_3$ | 1 | N | White crystal 179–180 | 0.93(s, 3H), 1.07(s, 3H), 0.73–2.03(m, 8H), 2.70–2.97 (m, 1H), 3.47(s, 1H), 4.48(s, 2H), 6.87(d, 2H, J=9Hz), 7.17(d, 2H, J=9Hz), 7.90(s, 1H), 8.17(s, 1H) |
| I-2 | CH$_3$ | H | 1 | N | Viscous oily product | 0.53–3.73(m, 10H), 0.78, 1.07(2d, 3H, J=6Hz, 4Hz), 4.17(bs, 1H), 4.43(bs, 2H), 6.87–7.43(m, 4H) 8.00, 8.07(2s, 1H), 8.18, 8.37(2s, 1H) |
| I-3 | CH$_3$ | H | 1 | CH | White crystal 116–119 | 0.63–3.37(m, 11H), 0.82, 1.08(2d, 3H, J=6Hz, 4Hz), 4.10, 4.17(2s, 2H), 6.83–7.37(m, 6H), 7.57, 7.67(2s, 1H) |
| I-4 | CH$_3$CH$_2$ | H | 1 | N | White crystal 109–110 | 0.65–3.48(m, 15H), 3.72(s, 1H), 4.32, 4.42(2s, 2H) 6.78–7.32(m, 4H), 7.88, 7.93(2s, 1H), 7.98, 8.13(2s, 1H) |
| I-5 | CH$_3$CH$_2$ | H | 1 | CH | White crystal 117–121 | 0.63–3.37(m, 16H), 4.10, 4.33(2s, 2H), 6.87–7.37(m, 6H), 7.53, 7.63(2s, 1H) |

TABLE I-continued

An Azole-substituted Cycloalkanol Derivative of the Formula (I)

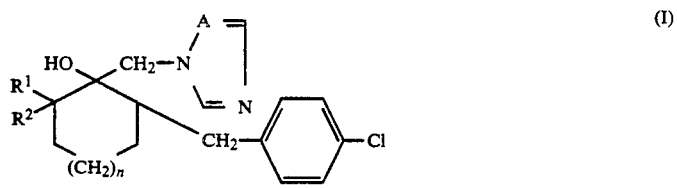

(I)

| Compound No. | Indication in Formula (I) R¹ | R² | n | A | Physical Properties (below line is m.p. in °C.) | NMR Spectrum Data (CDCl₃ δ ppm) |
|---|---|---|---|---|---|---|
| I-6 | $CH_3$ | $CH_3$ | 2 | N | Viscous oily product | 1.05(s, 3H), 1.08(s, 3H), 0.95–2.33(m, 10H), 2.68–3.08(m, 1H), 3.47(bs, 1H), 4.30(d, 1H, J=14Hz), 4.63(d, 1H, J=14Hz), 6.93(d, d, 2H, J=9Hz), 7.20 (d, 2H, J=9Hz), 7.98(s, 1H), 8.25(s, 1H) |
| I-7 | $CH_3$ | H | 2 | N | Viscous oily product | 0.75–1.18(m, 3H), 1.18–3.55(m, 12H), 4.32, 4.38(2bs, 2H), 6.92–7.42(m, 4H), 7.98(s, 1H) 8.22, 8.28(2s, 1H) |
| I-8 | $CH_3$ | H | 2 | CH | Viscous oily product | 0.75–1.17(m, 3H), 1.17–3.40(m, 12H), 4.07, 4.12(2s, 2H), 6.90–7.70(m, 7H) |
| I-9 | $CH_3CH_2$ | H | 2 | N | Viscous oily product | 0.57–3.30(m, 17H), 3.57(bs, 1H), 4.27, 4.33(2s, 2H), 6.80–7.17(m, 4H), 7.87(s, 1H), 8.10, 8.20(s, 1H) |
| I-10 | $CH_3CH_2$ | H | 2 | CH | Viscous oily product | 0.55–3.40(m, 17H), 4.08(s, 3H), 6.82–7.35(m, 6H), 7.53, 7.62(2s, 1H) |

TABLE II

An Oxirane Derivative of the Formula (II)

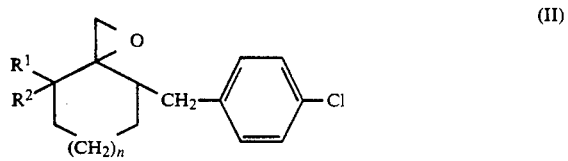

(II)

| Compound No. | Indication in Formula (II) R¹ | R² | n | Synthetic Method | Physical Properties | NMR Spectrum Data (CDCl₃ δ ppm) |
|---|---|---|---|---|---|---|
| II-1 | $CH_3$ | $CH_3$ | 1 | A | Oily product | 0.77(s, 3H), 1.07(s, 3H), 0.97–2.87(m, 9H), 2.67(m, 2H), 6.92(d, 2H, J=9Hz), 7.13 (d, 2H, J=9Hz), |
| II-2 | $CH_3$ | H | 1 | B | Oily product | 0.60–3.03(m, 10H), 0.75 (d, 3H, J=6Hz), 2.63, 2.77 (2s, 2H), 7.00(d, 2H, J=8Hz), 7.23(d, 2H, J=8Hz) |
| II-3 | $CH_3CH_2$ | H | 1 | B | Oily product | 0.63–3.00(m, 15Hz), 2.58, 2.77 (2s, 2H), 7.03(d, 2H, J=8Hz), 7.23(d, 2H, J=8Hz) |
| II-4 | $CH_3$ | $CH_3$ | 2 | B | Oily product | 0.73, 0.78(2s, 3H), 0.93(s, 3H), 0.63–2.93(m, 13H), 6.92–7.37(m, 4H) |
| II-5 | $CH_3$ | H | 2 | B | Oily product | 0.78, 0.85(2d, 3H, J=6Hz), 1.03–2.95(m, 12H), 2.55, 2.62(2s, 2H), 7.10(d, 2H, J=8Hz), 7.30(d, 2H, J=8Hz) |
| II-6 | $CH_3CH_2$ | H | 2 | B | Oily product | 0.63–3.17(m, 17H), 2.20, 2.27 (2s, 2H), 6.90–7.33(m, 4H) |

In the above Table, Synthetic Methods A and B are the methods described in page 16, item (2)(a) and page 17, item (2)(b), respectively.

TABLE III

A Methylenecycloalkane Derivative of the Formula (III)

$$\text{(III)}$$

| Compound No. | Indication in Formula (III) R$^1$ | R$^2$ | n | Physical Properties | NMR Spectrum Data (CDCl$_3$ δ ppm) |
|---|---|---|---|---|---|
| III-1 | CH$_3$ | H | 1 | Oily product | 0.72–3.35(m, 13H), 4.65, 4.78 (2bs, 2H), 7.02–7.12(m, 4H) |
| III-2 | CH$_3$CH$_2$ | H | 1 | Oily product | 0.50–3.23(m, 15H), 4.60, 4.67 (2bs, 2H), 6.87–7.37(m, 4H) |
| III-3 | CH$_3$ | CH$_3$ | 2 | Oily product | 0.75(s, 3H), 1.02(s, 3H), 0.72–2.92(m, 11H), 4.83(d, 2H, J=3Hz), 6.93(d, 2H, J=9Hz), 7.13 (d, 2H, J=9Hz) |
| III-4 | CH$_3$ | H | 2 | Oily product | 0.77–2.93(m, 12H), 0.93, 1.05(2d, 3H, J=7Hz, 6Hz), 4.47–4.57, 4.63–4.87(2m, 2H), 6.77–7.20(m, 4H) |
| III-5 | CH$_3$CH$_2$ | H | 2 | Oily product | 0.50–2.97(m, 14H), 0.78(t, 3H, J=7Hz), 4.63–4.90(m, 2H), 6.88–7.30(m, 4H) |

TABLE IV

A Cycloalkanone Derivative of the Formula (IV)

$$\text{(IV)}$$

| Compound No. | Indication in Formula (IV) R$^1$ | R$^2$ | n | Physical Properties | NMR Spectrum Data (CDCl$_3$ δ ppm) |
|---|---|---|---|---|---|
| IV-1 | CH$_3$ | CH$_3$ | 1 | Oily product | 1.03(s, 3H), 1.17(s, 3H), 0.90–3.33(m, 9H), 7.07(d, 2H, J=9Hz), 7.27(d, 2H, J=9Hz) |
| IV-2 | CH$_3$ | H | 1 | Oily product | 0.85–3.45(m, 10H), 1.00(d, 3H, J=6Hz), 6.98–7.45(m, 4H) |
| IV-3 | CH$_3$CH$_2$ | H | 1 | Oily product | 0.63–3.40(m, 15Hz), 6.93–7.37(m, 4H) |
| IV-4 | CH$_3$ | CH$_3$ | 2 | Oily product | 0.68(s, 3H), 0.98(s, 3H), 0.55–3.28(m, 11H), 6.92(d, 2H, J=9Hz), 7.10(d, 2H, J=9Hz) |
| IV-5 | CH$_3$ | H | 2 | Oily product | 0.65–3.22(m, 12H), 0.82(d, 3H, J=7Hz), 6.95(d, 2H, J=8Hz), 7.15(d, 2H, J=8Hz) |
| IV-6 | CH$_3$CH$_2$ | H | 2 | Oily product | 0.43–3.23(m, 17H) 6.87–7.33(m, 4H) |

TABLE V

A Cycloalkanecarboxylic Acid Ester Derivative of the Formula (V)

$$\text{(V)}$$

| Compound No. | Indication in Formula (V) R$^1$ | R$^2$ | R | n | Physical Properties | NMR Spectrum Data (CDCl$_3$ δ ppm) |
|---|---|---|---|---|---|---|
| V-1 | CH$_3$ | CH$_3$ | CH$_3$CH$_2$ | 1 | Oily product | 1.07(s, 6H), 2.07–2.63(m, 6H), 1.20(t, 3H, J=7Hz), 2.82 (d, 1H, J=14Hz), 3.32(d, 1H, |

TABLE V-continued

A Cycloalkanecarboxylic Acid Ester Derivative of the Formula (V)

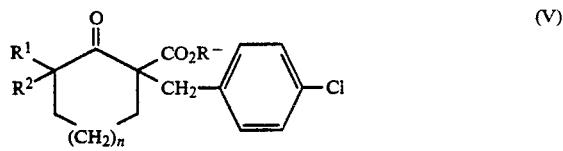

(V)

| Compound No. | Indication in Formula (V) R¹ | R² | R | n | Physical Properties | NMR Spectrum Data (CDCl₃ δ ppm) |
|---|---|---|---|---|---|---|
| | | | | | | J=14Hz), 4.07(q, 2H, J=7Hz), 6.98(d, 2H, J=9Hz), 7.23(d, 2H, J=9Hz) |
| V-2 | CH₃ | CH₃ | CH₃ | 2 | Oily product | 1.08(s, 3H), 1.17(s, 3H), 0.82–2.28(m, 8H), 2.93(d, 1H, J=14 Hz), 3.27(d, 1H, J=14Hz), 3.65(s, 3H), 7.00(d, 2H, J=9Hz), 7.25(d, 2H, J=9Hz) |
| V-3 | CH₃ | H | CH₃ | 2 | Oily product | 0.98(d, 3Hz, J=6Hz), 0.88–2.48(m, 9H), 3.15(s, 2H), 3.75(s, 3H), 7.05(d, 2H, J=9Hz), 7.28(d, 2H, J=9Hz) |
| V-4 | CH₃CH₂ | H | CH₃ | 2 | Oily product | 0.57–3.43(m, 16H), 3.63, 3.70(2s, 3H), 6.87–7.20(m, 4H) |

TABLE VI

A Cycloalkanecarboxylic Acid Ester Derivative of the Formula (VII)

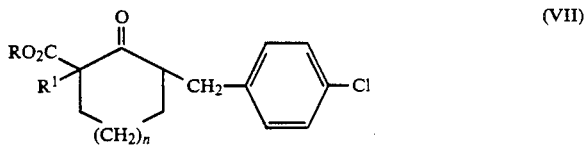

(VII)

| Compound No. | Indication in Formula (VII) R¹ | R | n | Physical Properties | NMR Spectrum Data (CDCl₃ δ ppm) |
|---|---|---|---|---|---|
| VII-1 | CH₃ | CH₃ | 1 | Oily product | 0.70–3.40(m, 9H), 1.27, 1.43 (2s, 3H), 3.65, 3.70(2s, 3H), 6.93–7.37(m, 4H) |
| VII-2 | CH₃CH₂ | CH₃ | 1 | Oily product | 0.57–3.33(m, 14H), 3.67, 3.73(2s, 3H), 6.93–7.40(m, 4H) |

TABLE VII 3-(4-chlorobenzyl)-2-oxocycloalkanecarboxylic acid alkyl ester of the Formula (VIII)

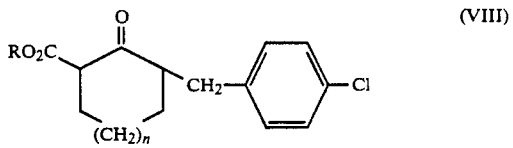

(VIII)

| Compound No. | Indication in Formula (VII) R | n | Physical Properties | NMR Spectrum Data (CDCl₃ δ ppm) |
|---|---|---|---|---|
| VIII-1 | CH₃ | 1 | Oily product b.p. at 2 mmHg 175–180° C. | 0.70–3.47(m, 10H), 3.67, 3.73(2s, 3H), 6.93–7.40(m, 4H) |

NMR spectrum of the compounds shown in the above Tables I to VII are measured by using TMS as a standard and shown by the following symbols:
S . . . singlet,
d . . . doublet,
t . . . triplet,
q . . . qualtet,
m . . . multiplet,
b . . . broad line,
J = coupling constant (unit: Hz)

Next, the process for producing the azole-substituted cycloalkanol derivatives (I) will be explained. First, the present process is described concisely.

(1) Reaction of obtaining a cycloalkanone derivative (IV) from 1-(4-chlorobenzyl)-2-oxocycloalkanecarboxylic acid alkyl ester (VI):

(a) 1-(4-chlorobenzyl)-2-oxocycloalkanecarboxylic acid alkyl ester (VI) is alkylated to cycloalkanecarboxylic acid ester derivative (V) and subsequently subjecting to the resulting derivative to hydrolysis and decarboxylation to obtain cycloalkanone derivative (IV):

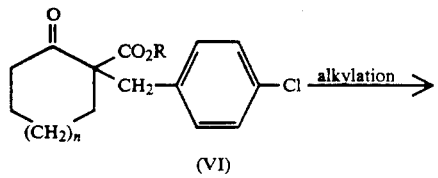
(VI)

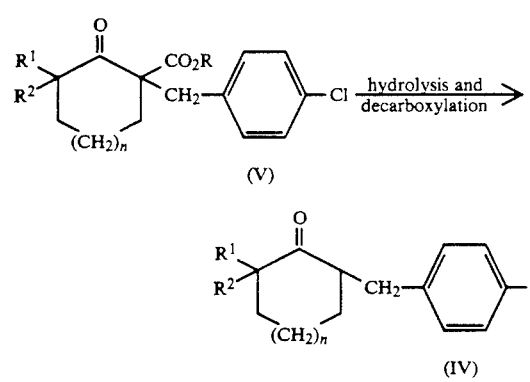
(V)

(IV)

(b) As the other method, 1-(4-chlorobenzyl)-2-oxocycloalkanecarboxylic acid alkyl ester (VI) is subjected to isomerization [see J. Org. Chem., 29, 2781 (1964)] to 3-(4-chlorobenzyl)-2-oxocycloalkanecarboxylic acid alkyl ester (VIII), and the resulting derivative is alkylated to give cycloalkanecarboxylic acid ester derivative (VII) and subsequently subjecting to hydrolysis and decarboxlation to obtain cycloalkanone derivative (IV) wherein $R^1$ is a lower alkyl group and $R^2$ is a hydrogen atom.

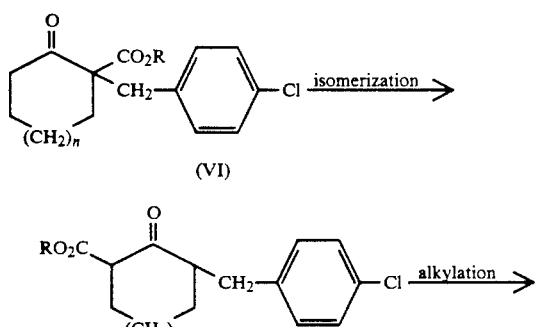
(VI)

(VIII)

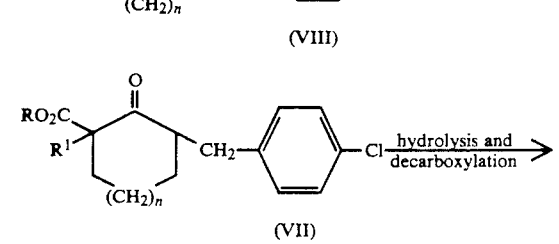
(VII)

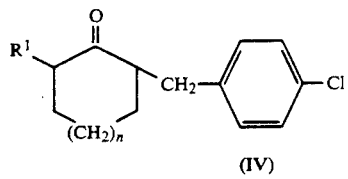
(IV)

(2) Reaction of obtaining an oxirane derivative (II) from a cycloalkanone derivative (IV):

(a) A cycloalkanone derivative (IV) is reacted with dimethyloxosulfonium methylide or dimethylsulfonium methylide in the presence of a diluent to obtain an oxirane derivative (II) [see Org. Synth., 49, 78 (1969)].

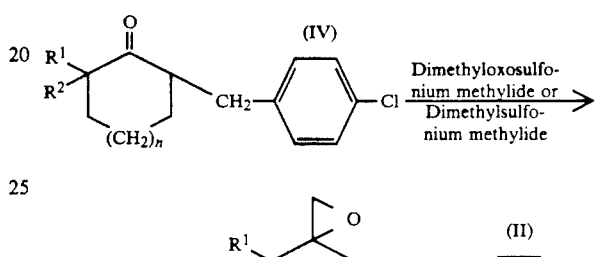

(II)

(b) As the other method, a cycloalkanone derivative (IV) is subjected to Wittig reaction to obtain a methylene cycloalkane derivative (III) [see J. Org. Chem., 28, 1128 (1963)], and from this derivative (III), an oxirane derivative (II) can be obtained by the epoxidation reaction [see Org. Synth., Coll. (4), 552 (1963) and 49, 62 (1969)].

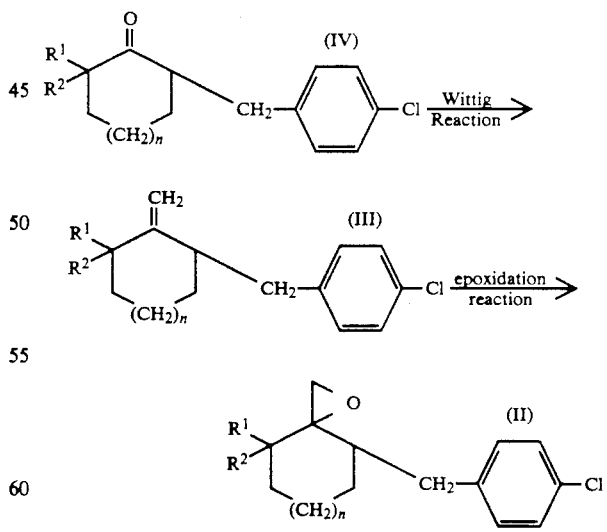

(3) Reaction to obtain an azole-substituted cycloalkanol derivative (I) from an oxirane derivative (II):

By reacting an oxirane derivative (II) and 1,2,4-triazole or imidazole represented by the following formula (IX):

wherein M represents a hydrogen atom or an alkali metal, and A represents a nitrogen atom or a CH group, an azole-substituted cycloalkanol derivative (I) which is the title compound can be obtained as follow:

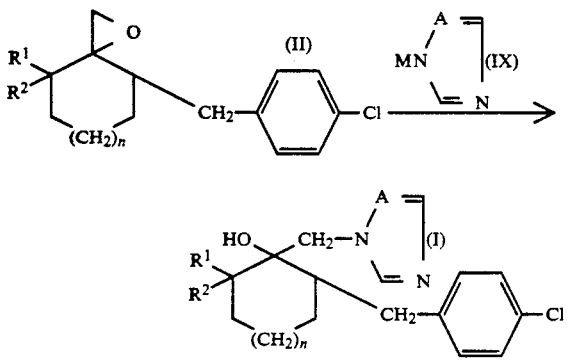

In the above preparation process, an organic solvent is often used as a diluent, and the reaction is sometimes carried out in the presence of a base or an acid in addition to the diluent, depending on the reaction.

The diluent may be exemplified by hydrocarbons such as benzene, toluene, xylene and hexane; halogenated hydrocarbons such as methylene chloride, chloroform and carbon tetrachloride; alcohols such as methanol and ethanol; ethers such as diethyl ether, diisopropyl ether and tetrahydrofuran; and acetonitrile, acetone, dimethylformamide, dimethylsulfoxide and N-methyl-2-pyrrolidone as the others.

The base to be used may be exemplified by carbonates of an alkali metal such as sodium carbonate and potassium carbonate; hydroxides of an alkali metal such as sodium hydroxide and potassium hydroxide; alkoxides of an alkali metal such as sodium methoxide, sodium ethoxide and potassium t-butoxide; alkali metal hydrogen compounds such as sodium hydride and potassium hydride; organometal compounds of an alkali metal such as n-butyl lithium; and triethylamine and pyridine as the others.

Also, the acid may be exemplified by inorganic acids such as hydrochloric acid, hydrobromic acid, hydroiodic acid and sulfuric acid; and organic acids such as formic acid, acetic acid, butyric acid and p-toluenesulfonic acid.

In the following, each reaction in the above preparation processes will be explained in more detail.

In the above item (1)-(a) for preparing cycloalkane carboxylic acid ester derivative (V) by alkylating 1-(4-chlorobenzyl)-2-oxocycloalkanecarboxylic acid alkyl ester (VI), the reaction can be preferably carried out by reacting a lower alkyl halide to the compound of the formula (VI) dissolved in an above diluent in the presence of an above base. Also, in the case of monoalkylation, 1.0 to 1.2 equivalent amount of a lower alkyl halide and in the case of dialkylation, 2.0 to 3.0 equivalent amount of a lower alkyl halide to the compound of the formula (VI) is preferably reacted, respectively. The reaction temperature in these cases can be applied any temperature from the solidifying point of the diluent to the boiling point of the same.

In the above item (1)-(b) for preparing a 3-(4chlorobenzyl)-2-oxocycloalkanecarboxylic acid alkyl ester (VIII) by isomerizing the compound of the formula (VI), the reaction can be preferably carried out by reacting the compound of the formula (VI) dissolved in an above diluent (alcohols are particularly preferred) with an aforesaid base (e.g. alkoxide of an alkali metal) and evaporating the diluent. The reaction temperature in the above reaction can be applied any temperature from the solidifying point of the diluent to the boiling point of the same.

In the above items (1)-(a) and (b) for preparing a cycloalkanone derivative (IV) by subjecting a cycloalkanecarboxylic acid ester derivative (V) or (VII) to hydrolysis and decarboxylation, the reaction can be preferably carried out by subjecting a compound of the formula (V) or a compound of the formula (VII) to hydrolysis and decarboxylation in the presence of an aforesaid base under stirring for 2 to 45 hours. The reaction temperature in these cases can be applied any temperature from the solidifying point of the diluent to the boiling point of the same, but the temperature of 100° to 120° C. is particularly preferred.

In the above item (2)-(a) for preparing an oxirane derivative (II) from a cycloalkanone derivative (IV), the reaction can be preferably carried out by reacting a compound of the formula (IV) with 1.0 to 2.0 equivalents of dimethyloxosulfonium methylide or dimethylsulfonium methylide prepared by mixing trimethylsulfoxonium iodide or trimethylsulfonium iodide and an above base (e.g. sodium hydride) with equiamounts in an aforesaid diluent (dimethylsulfoxide is particularly preferred as a diluent) at 25° to 100° C. for 1 to 40 hours.

Also, in the reaction of the above item (2)-(b) for preparing a compound of the formula (II) from a compound of the formula (IV) via a methylenecycloalkane derivative (III), it can be preferably carried out by adding a compound of the formula (IV) to methylenetriphenylphosphorane (Wittig reagent) prepared by mixing an equiamount of an aforesaid base (e.g. sodium hydride) and methyltriphenylphosphonium halide in an aforesaid diluent (particularly dimethylsulfoxide is preferred) to form a compound of the formula (III), and after separating the compound, dissolving it again in the diluent, adding an organic peracid, such as peracetic acid, perbenzoic acid and m-chloroperbenzoic acid, or hydrogen peroxide to effect epoxidation reaction at the temperature range between the room temperature and the boiling point of said diluent to give an oxirane derivative (II).

Next, in the reaction of preparing an azole-substituted cycloalkanol derivative (I) which is an objective compound of the present invention by reacting an azole compound (IX) to a compound of the formula (II), it can be preferably carried out by adding 0.5 to 1.0 equivalent amount of a compound of the formula (II) to a compound of the formula (IX) dissolved in an aforesaid diluent, if necessary, in the presence of an aforesaid base, or contrary thereto, by adding 1.0 to 2.0 equivalent amount of an azole compound of the formula (IX) to a compound of the formula (II) dissolved in an aforesaid diluent, and stirring for 1 to 6 hours. The reaction temperature can be applied any temperature from the solidifying point of the diluent to the boiling point of the same, but the temperature of 0° to 100° C. is particularly preferred. Also, when M in an azole compound of the formula (IX) is a hydrogen atom, the presence of an aforesaid base is particularly preferred.

After completion of the above reaction, the reaction mixture obtained by the reaction is cooled and then extracted with an organic solvent such as ethyl acetate, chloroform or benzene in an iced water. The organic layer is separated and then washed with water and dried, and the solvent is evaporated under reduced pressure. The obtained residue is subjected to a purification treatment to obtain an aimed compound. The purification can be carried out by subjecting the residue to a recrystallization or applying it to a silica gel column chromatography.

Next, availability of the azole-substituted cycloalkanol derivative represented by the formula (I) according to the present invention as an active ingredient for agricultural and horticultural fungicide will be explained.

The azole-substituted cycloalkanol derivative according to the present invention show wide fungicidal effects against the plant diseases as shown below as examples.

*Pyricularia oryzae* of rice, *Cochliobolus miyabeanus* of rice, *Xanthomonas oryzae* of rice, *Rhizoctonia solani* of rice, *Helminthosporium sigmoideum* of rice, *Gibberella fujikuroi* of rice, *Podosphaera leucotricha* of apple, *Venturia inaequalis* of apple, *Monilinia mali* of apple, *Alternaria mari* of apple, *Valsa mali* of apple, *Alternaria kikuchiana* of pear, *Phyllactinia pyri* of pear, *Gymnosporangium asiaticum* of pear, *Venturia nashicola* of pear, *Uncinula necator* of grape, *Phakopsora ampelopsidis* of grape, *Glomerella cingulata* of grape, *Erysiphe graminis* f. sp. *hordei* of barley, *Rhynchosporium secalis* f. sp. *hordei* of barley, *Puccinia graminis* of barley, *Puccinia striiformis* of barley, *Puccinia recondita* of wheat, *Septoria tritici* of wheat, *Puccinia striiformis* of wheat, *Erysiphe graminis* f. sp. *tritici* of wheat, *Sphaerotheca fuliginca* of cucurbitaceae, *Colletotrichum lagenarium* of cucurbitaceae, *Fusarium oxysporum* f. sp. *niveum* of water melon, *Fusarium oxysporum* f. sp. *cucumerinum* of cucumber, *Fusarium oxysporum* f. sp. *raphani* of white radish, *Erysiphe cichoracearum* of tomato, *Alternaria solani* of tomato, *Erysiphe cichoracearum* of egg plant, *Sphaerotheca humuli* of strawberry, *Erysiphe cichoracearum* of tobacco, *Alternaria longipes* of tobacco, *Cercospora beticola* of sugar beet, *Alternaria solani* of potato, *Septoria glycines* of soybean, *Cercospora kikuchi* of soybean, *Monilinia fructicola* of stone fruit trees, and *Botrytis cinerea* and *Sclerotinia sclerotiorum* of various crops.

For applying an azole-substituted cycloalkanol derivative represented by the above formula (I) as a fungicide, it can be advantageously used as it is or mixing with a carrier (or a diluent) in the form of powders, wettable powders, granules, emulsions and liquids. Further, if necessary, it is, of course, possible to make the effect more certain by adding adjuvant such as spreading agents, emulsifiers, wetting agents and fixing agents in addition to the above carriers.

Since the present compounds have 1,2,4-triazole ring or imidazole ring, it can be used in the form of a salt of an inorganic acid or an organic acid, or of a metal complex salt.

Also, since in the present compounds, an azolylmethyl group, a 4-chlorobenzyl group and a lower alkyl group are bonded to the cylcloalkane ring, geometric isomers of cis-isomer and trans-isomer and optical isomers can be present, but in the present invention, all the respective isomer alone and a mixture of each isomer with an optional ratio are included.

Accordingly, it should be understood that the agricultural and horticultural fungicide according to the present invention includes those containing respective isomer alone or a mixture thereof as an active ingredient.

EXAMPLES

In the following, specific preparation examples of the azole-substituted cycloalkanol derivatives according to the present invention and specific examples of the agricultural and horticultural fungicide utilizing said derivatives as an active ingredient are shown to explain the effect of the present invention.

First, preparation examples of an azole-substituted cycloalkanol derivative represented by the formula (I) and those of each intermediate for preparing the same are shown below.

EXAMPLE 1

Preparation of 1-(4-chlorobenzyl)-3-ethyl-2-oxocycloheptane carboxylic acid methyl ester [Compound (V-4) of Table V].

1.63 g of sodium hydride (60% oily sodium hydride washed with dried hexane) were added to 100 ml of dried tetrahydrofuran and stirred under helium atmosphere and 20.0 g of 1-(4-chlorobenzyl)-2-oxocycloheptane carboxylic acid methyl ester was added and stirred at room temperature for 20 minutes. Then, the temperature was raised to 40° C. and 10.6 g of ethyl iodide was gradually added for 50 minutes and further stirred at 60° C. for 6.5 hours.

The reaction mixture obtained was allowed to stand for cooling, poured into iced water, extracted with benzene and obtained organic layer was successively washed with water and a saline solution. The layer was dried over dried sodium sulfate and distilled off the solvent under reduced pressure.

The residue obtained was purified with a silica gel column chromatography and obtained 19.7 g of the title compound.

EXAMPLE 2

Preparation of 2-(4-chlorobenzyl)-7-ethyl-1-cycloheptanone [Compound (IV-6) of Table IV].

To 19.5 g of 1-(4-chlorobenzyl)-3-ethyl-2-oxocycloheptanecarboxylic acid methyl ester were added 50 ml of a 47% hydrobromic acid and 70 ml of acetic acid and the mixture was vigorously stirred at 120° C. for 15 hours.

The resulting reaction mixture was allowed to stand for cooling, poured into iced water and extracted with benzene to obtain an organic layer. Said organic layer was successively washed with an aqueous sodium hydrogen carbonate solution and saline solution, dried over sodium sulfate and the solvent was removed under reduced pressure.

The obtained residue was applied to a silica gel column chromatography for purification and obtained 8.3 g of the title compound.

EXAMPLE 3

Preparation of 3-(4-chlorobenzyl)-2-oxocyclohexanecarboxylic acid methyl ester [Compound (VIII-1) of Table VII].

In 300 ml of dried methanol were dissolved 50 g of 1-(4-chlorobenzyl)-2-oxocyclohexanecarboxylic acid ethyl ester and 50 g of a 28% sodium methoxide methanol solution was added thereto, and the mixture was refluxed for 3 hours under heating. Next, after removing 150 ml of methanol used, 400 ml of dried toluene were added to the reaction mixture and the remaining methanol was removed by azeotropic distillation with toluene.

The residual material was poured into diluted acetic acid at 0° C. and extracted with benzene. After the organic layer was successively washed with water, an aqueous sodium hydrogen carbonate solution and saline solution, the layer was dried over dried sodium sulfate and the solvent was removed under a reduced pressure.

The obtained residue was applied to a silica gel column chromatography for purification to obtain 22.9 g of the title compound. The boiling point of the product was 175° to 180° C. at 2.0 mmHg.

EXAMPLE 4

Preparation of 3-(4-chlorobenzyl)-1-ethyl-2-oxocyclohexanecarboxylic acid methyl ester [Compound (VII-2) in Table VI].

In 10 ml of dried dimethylformamide was added 660 mg of sodium hydride (60% oily sodium hydride washed with dried hexane) in a helium atmosphere under stirring and then 8.0 g of 3-(4-chlorobenzyl)-2-oxocyclohexanecarboxylic acid methyl ester [Compound (VIII-1)] was added to the mixture over 20 minutes and the mixture was stirred at room temperature for further one hour. Next, 5.5 g of ethyl iodide was added over 10 minutes and the mixture was stirred at room temperature for 1.5 hours.

The resulting reaction mixture was poured into iced water and extracted with benzene to obtain an organic layer. The layer successively washed with water and a saline solution, dried over dried sodium sulfate and the solvent was removed under reduced pressure to obtain 9.9 g of the title compound.

EXAMPLE 5

Preparation of 8-(4-chlorobenzyl)-4,4-dimethyl-1-oxaspiro[2.5]Octane. [Compound (II-1) of Table II].

In 20 ml of dried dimethylsulfoxide was added 840 mg of sodium hydride (60% oily sodium hydride washed with dried hexane) in a helium atmosphere under stirring, and then 7.7 g of trimethyloxosulfonium iodide was added to the mixture and the mixture was stirred at room temperature for one hour. Next, 4.5 g of 6-(4-chlorobenzyl)-2,2-dimethylcyclohexanone [Compound (IV-1) in Table IV] was added and the mixture was stirred at 70° C. for 2 hours.

The resulting reaction mixture was allowed to stand for cooling, poured into iced water and extracted with benzene to obtain an organic layer. The layer was washed with a saline solution, dried over dried sodium sulfate and the solvent was removed under reduced pressure.

The obtained residue was applied to a silica gel column chromatography to obtain 2.7 g of the title compound.

EXAMPLE 6

Preparation of 2-(4-chlorobenzyl)-6-methl-1-methylenecyclohexane [Compound (III-1) in Table III].

In 20 ml of dried dimethylsulfoxide was added 540 mg of sodium hydride (60% oily sodium hydride washed with dried hexane) in a helium atmosphere under stirring and the mixture was further stirred at 70° C. for 5 minutes. The mixture was cooled with iced water and then 8.0 g of methyltriphenylphosphonium bromide was added to the mixture and the mixture was stirred at room temperature for 30 minutes. Next, 2.8 g of 2-(4-chlorobenzyl)-6-methylcyclohexanone [Compound (IV-2) in Table IV] was added and the mixture was stirred at room temperature for one hour.

The resulting reaction mixture was allowed to stand for cooling, poured into iced water and extracted with hexane to obtain an organic layer. Solid material of triphenylphosphin oxide in the organic layer was filtered off and said organic layer was washed with a saline solution, dried over dried sodium sulfate and the solvent was removed under reduced pressure.

The obtained residue was applied to a silica gel column chromatography for purification to obtain 2.2 g of the title compound.

EXAMPLE 7

Preparation of 9-(4-chlorobenzyl)-4,4-dimethyl-1-oxaspiro[2.6]-nonane [Compound (II-4) in Table II].

In 5 ml of chloroform was dissolved 340 mg of 7-(4-chlorobenzyl)-2,2-dimethyl-1-methylenecycloheptane [Compound (III-3) in Table III), and then 450 mg of m-chloroperbenzoic acid was added to the mixture over 10 minutes and the mixture was stirred at room temperature for one hour. Next, 385 mg of calcium hydroxide was added and the mixture was stirred at room temperature for 10 minutes.

Precipitated solid materials were filtered off and the chloroform layer in the filtrate was condensed to obtain a colorless oily substance. The resulting oily substance was applied to a silica gel column chromatography for purification to obtain 320 mg of the title compound.

EXAMPLE 8

Preparation of 2-(4-chlorobenzyl)-7-ethyl-1-(1H-1,2,4-triazol-1-ylmethyl)-1-cycloheptanol. [Compound (I-9) in Table I].

In 40 ml of dried dimethylformamide was added 350 mg of sodium hydride (60% oily sodium hydride washed with dried hexane) in a helium atmosphere under stirring and then 1.0 g of 1H-1,2,4-triazole was added and the mixture was stirred at room temperature until forming had stopped.

To the solution obtained, 2.0 g of 4-(4-chlorobenzyl)-9-ethyl-1-oxaspiro[2.6]nonane [Compound (II-6) in Table II] was added and the mixture was stirred at 90° C. for 10 hours.

The resulting reaction mixture was allowed to stand for cooling, poured into iced water and extracted with ethyl acetate to obtain an organic layer. The layer was washed with water, dried over dried sodium sulfate and the solvent was removed under reduced pressure.

The obtained residue was applied to a silica gel column chromatography for purification and crystallized to obtain 0.75 g of the title compound.

EXAMPLE 9

Preparation of 2-(4-chlorobenzyl)-6-ethyl-1-(1H-1,2,4-imidazol-1-ylmethyl)-1-cyclohexanol. [Compound (I-5) in Table I].

In 4 ml of dried dimethylformamide was added 109 mg of sodium hydride (60% oily sodium hydride washed with dried hexane) in a helium atmosphere under stirring and then 310 mg of 1H-imidazole was added and the mixture was stirred at room temperature until forming had stopped.

To the resulting solution was added 600 mg of 4-(4-chlorobenzyl)-8-ethyl-1-oxaspiro[2.5]octane [Compound (II-3) in Table II] and the mixture was stirred at 70° C. for 1.5 hours.

The resulting reaction mixture was allowed to stand for cooling, poured into iced water and extracted with ethyl acetate to obtain an organic layer. The layer was washed with water, dried over dried sodium sulfate and the solvent was removed under reduced pressure.

The obtained residue was applied to a silica gel column chromatography for purification and crystallized to obtain 584 mg of the title compound. The melting point of the compound was 117° to 121° C.

Next, preparation examples for practically using the compounds of the present invention will be described, but amounts and kinds of the effective components to be used, kinds of the carrier (including diluents) and adjuvants, and mixing ratio thereof are not limited by the following examples or around thereof and can be modified with a wide range.

EXAMPLE 10

Powders

3 Parts by weight of the present compound (I-9), 40 parts by weight of clay and 57 parts by weight of talc were mixed and pulverized to use as powders.

EXAMPLE 11

Wettable Powder.

50 Parts by weight of the present compound (I-4), 5 parts by weight of Lignosulfonate, 3 parts by weight of an alkylsulfonate and 42 parts by weight of diatomaceous earth were mixed and pulverized to prepare wettable powders and used as an aqueous suspension.

EXAMPLE 12

Granules.

5 Parts by weight of the present compound (I-6), 43 parts by weight of bentonite, 45 parts by weight of clay and 7 parts by weight of Lignosulfonate were mixed uniformly and kneaded by adding water and then extruded by extrusion granulator in a shape of granule and dried to obtain grannules.

EXAMPLE 13

Emulsion.

25 Parts by weight of the present compound (I-10), 10 parts by weight of polyoxyethylenealkylallyl ether, 3 parts by weight of polyoxyethylenesorbitol monolaurate and 62 parts by weight of xylene were mixed uniformly and make a solution to obtain an emulsion concentrate.

Next, in order to prove availability of the compound of the present invention for agricultural and horticultural fungicide as effective ingredients, fungicidal test results using various preparations are shown in the following examples.

EXAMPLE 14

Preventive Test of Wheat Brown Rust Disease.

To two-leaved state young seedlings of wheat (kind: NORIN No. 64; 16 seedlings/pot, 3 pots/region) planted by using an unglazed pot having a diameter of 10 cm were sprayed with each 5 ml of aqueous suspensions of wettable powders prepared according to Example 11 using various azole derivatives of the present invention and being diluted in a predetermined concentration. After drying the sprayed leaves by air, a suspension of summer spore of wheat brown rust disease collected from contracted leaves was sprayed to inoculate the fungi and the leaves were maintained at 20° to 23° C. under high humidity for 24 hours. Thereafter, they were allowed to stand in a greenhouse and after 7 to 10 days of inoculation, spotted surface ratio by the disease was evaluated and the control value was calculated with the following equation:

$$\text{Control value (\%)} = \left(1 - \frac{\text{Spotted surface ratio of sprayed region}}{\text{Spotted surface ratio of non-sprayed region}}\right) \times 100$$

The results are shown in Table VIII.

TABLE VIII

| Compound Tested (Number in Table I) | Concentration of Spray (ppm) | Control Value (%) |
| --- | --- | --- |
| I-1 | 500 | 100 |
| I-2 | 500 | 100 |
| I-4 | 500 | 100 |
| I-6 | 500 | 100 |
| I-7 | 500 | 100 |
| I-9 | 500 | 100 |
| I-10 | 500 | 100 |
| Non-treated | — | 0 |

EXAMPLE 15

Preventive Test of Wheat Powdery Mildew.

To two-leaved state young seedlings of wheat (kind: NORIN No. 64; 16 seedlings/pot, 3 pots/region) planted by using an unglazed pot having a diameter of 10 cm were sprayed with each 5 ml of aqueous suspensions of wettable powders prepared according to Example 11 using various azole derivatives of the present invention and being diluted in a predetermined concentration. After drying the sprayed leaves by air, a suspension of spore of wheat powdery mildew disease collected from contracted leaves was sprayed to inoculate the fungi and the leaves were maintained at 20° to 23° C. under high humidity for 24 hours. Thereafter, they were allowed to stand in a greenhouse and after 7 to 10 days of inoculation, spotted surface ratio by the disease was evaluated and the control value was calculated with the following equation:

$$\text{Control value (\%)} = \left(1 - \frac{\text{Spotted surface ratio of sprayed region}}{\text{Spotted surface ratio of non-sprayed region}}\right) \times 100$$

The results are shown in Table IX.

TABLE IX

| Compound Tested (Number in Table I) | Concentration of Spray (ppm) | Control Value (%) |
| --- | --- | --- |
| I-1 | 500 | 100 |
| I-2 | 500 | 100 |
| I-3 | 500 | 100 |
| I-4 | 500 | 100 |
| I-5 | 500 | 100 |
| I-6 | 500 | 100 |
| I-7 | 500 | 100 |
| I-8 | 500 | 100 |
| I-9 | 500 | 100 |
| I-10 | 500 | 100 |

TABLE IX-continued

| Compound Tested (Number in Table I) | Concentration of Spray (ppm) | Control Value (%) |
|---|---|---|
| Non-treated | — | 0 |

EXAMPLE 16

Preventive Test of Kidney Bean Gray Mold.

To a first primary-leaved state kidney bean (kind: HONKINTOKI; 3 pots/region) planted by using an unglazed pot having a diameter of 10 cm were sprayed with each 5 ml of aqueous suspensions of wettable powders prepared according to Example 11 using various azole derivatives of the present invention and being diluted in a predetermined concentration. After drying the sprayed leaves by air, circle piece (4 mm in diameter) of agar containing fungi of gray mold previously cultivated by using a potato-sucrose agar medium at 20° C. for 3 days was directly adhered to the center of the leaf and the leaf was maintained at 20° to 22° C. under high humidity. Three days after the inoculation, spotted surface ratio by green bean gray mold was evaluated and the control value was calculated with the following equation:

$$\text{Control value (\%)} = \left(1 - \frac{\text{Spotted surface ratio of sprayed region}}{\text{Spotted surface ratio of non-sprayed region}}\right) \times 100$$

The results are shown in Table X.

TABLE X

| Compound Tested (Number in Table I) | Concentration of Spray (ppm) | Control Value (%) |
|---|---|---|
| I-1 | 500 | 100 |
| I-6 | 500 | 100 |
| I-9 | 500 | 100 |
| Non-treated | — | 0 |

EXAMPLE 17

Fungicidal Test Against Various Pathogenic Fungai.

This example shows the results tested fungicidal activity of the compound of azole derivatives according to the present invention against various plant pathogenic fungi.

Test Method.

The present compound was dissolved in dimethyl-sulfoxide to a predetermined concentration, and 0.6 ml of the solution and 60 ml of PSA medium at around 60° C. were thoroughly mixed in a conical flask of 100 ml in capacity, and poured into a culture dish to solidify them. On the other hand, sample fungi previously cultivated in a flat plate medium were punched by a cork bowler having a diameter of 4 mm and it was inoculated on the flat plate medium containing the above chemical. After inoculation, cultivation was carried out at an appropriate temperature for growth of each fungi for one to three days and growth of the fungi was measured by diameter of the colony. It was compared with that in the region without the chemicals and mycellia growth inhibition ratio was calculated according to the following equation:

$$R = 100 \times [1 - (dt/dc)]$$

wherein
R = mycellia growth inhibition ratio (%),
dc = diameter of colony on the flat plate without treatment
dt = diameter of colony on the flat plate treated with the chemicals The results were evaluated by 5 grades according to the following standard and shown in Table 11.

| Growth Inhibition Degree | |
|---|---|
| 5 | the inhibition ratio is not less than 90% to 100%; |
| 4 | the ratio is not less than 70% and less than 90%; |
| 3 | the ratio is not less than 40% and less than 70%; |
| 2 | the ratio is not less than 20% and less than 40%; |
| 1 | the ratio is less than 20%. |

The compounds A, B and C for the positive controls in this Example are the compounds (2), (3) and (4) in Table 1 of EP-A-0 324 646 and their formulae are as follows:

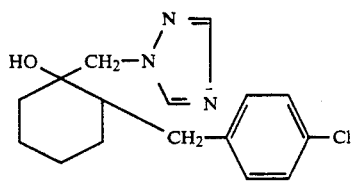
[A]

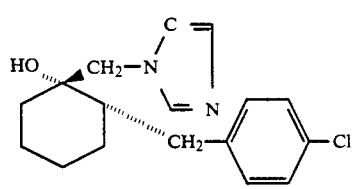
[B]

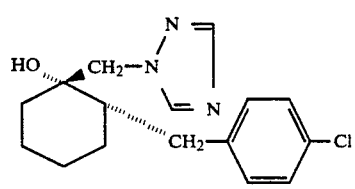
[C]

TABLE XI

| Compd. No. | μg/ml *1) | Fungi Tested | | | | | | | | | | | | | | | |
|---|---|---|---|---|---|---|---|---|---|---|---|---|---|---|---|---|---|
| | | P.o. | C.m. | G.f. | H.s. | R.s. | Bo.c. | S.s. | F.n. | F.c. | F.r. | C.l. | C.b. | M.f. | V.m. | A.k. | A.m. | G.c. |
| I-1 | 100 | 5 | 5 | 5 | 5 | 4 | 5 | 5 | 5 | 5 | 5 | 5 | 4 | 5 | 5 | 4 | 4 | 5 |
| I-2 | 100 | 5 | 5 | 5 | 5 | 5 | 5 | 5 | 5 | 5 | 5 | 5 | 5 | 5 | 5 | 5 | 5 | 5 |
| I-3 | 100 | 5 | 5 | 5 | 5 | 5 | 5 | 5 | 5 | 5 | 5 | 5 | 5 | 5 | 5 | 5 | 5 | 5 |
| I-4 | 100 | 5 | 5 | 5 | 5 | 5 | 5 | 5 | 5 | 5 | 5 | 5 | 5 | 5 | 5 | 5 | 5 | 5 |
| I-5 | 100 | 5 | 5 | 5 | 5 | 5 | 5 | 5 | 5 | 5 | 5 | 5 | 5 | 5 | 5 | 5 | 5 | 5 |
| I-6 | 100 | 5 | 5 | 5 | 5 | 4 | 5 | 5 | 5 | 5 | 5 | 5 | 5 | 5 | 5 | 4 | 5 | 5 |
| I-7 | 100 | 5 | 5 | 5 | 5 | 5 | 5 | 5 | 5 | 5 | 5 | 5 | 5 | 5 | 5 | 5 | 5 | 5 |
| I-8 | 100 | 5 | 5 | 5 | 5 | 5 | 5 | 5 | 5 | 5 | 5 | 5 | 5 | 5 | 5 | 5 | 5 | 5 |
| I-9 | 100 | 5 | 5 | 5 | 5 | 4 | 5 | 5 | 5 | 5 | 5 | 5 | 5 | 5 | 5 | 4 | 5 | 5 |

TABLE XI-continued

| Compd. No. | μg/ml *1) | Fungi Tested ||||||||||||||||
| --- | --- | --- | --- | --- | --- | --- | --- | --- | --- | --- | --- | --- | --- | --- | --- | --- | --- |
| | | P.o. | C.m. | G.f. | H.s. | R.s. | Bo.c. | S.s. | F.n. | F.c. | F.r. | C.l. | C.b. | M.f. | V.m. | A.k. | A.m. | G.c. |
| I-10 | 100 | 5 | 5 | 5 | 5 | 5 | 5 | 5 | 5 | 5 | 5 | 5 | 5 | 5 | 5 | 5 | 5 |
| A | 100 | 4 | 5 | 4 | 3 | 3 | 5 | 4 | 3 | 3 | 3 | 4 | 4 | 5 | 5 | 3 | 3 | 5 |
| B | 100 | 5 | 5 | 5 | 4 | 4 | 3 | 4 | 4 | 5 | 5 | 3 | 3 | 5 | 5 | 4 | 4 | 4 |
| C | 100 | 5 | 5 | 5 | 4 | 5 | 5 | 5 | 4 | 4 | 4 | 4 | 5 | 5 | 5 | 4 | 4 | 5 |

*1) Concentration of each compound

Abbreviations in Table XI mean the followings:

P.o.; *Pyricularia oryzae*
C.m.; *Cochliobolus miyabeanus*
G.f.; *Gibberella fujikroi*
H.s.; *Helminthosporium sigmoideum*
R.s.; *Rhizoctonia solani*
Bo.c.; *Botrytis cinerea*
S.s.; *Sclerotinia sclerotiorum*
F.n.; *Fusarium oxysporum* f.sp. *niveum*
F.c.; *Fusarium oxysporum* f. sp. *cucumerinum*
F.r.; *Fusarium oxysporum* f. sp. *raphani*
C.l.; *Colletotrichum lagenarium*
C.b.; *Cercospora beticola*
M.f.; *Monilinia fructicola*
V.m.; *Valsa mali*
A.k.; *Alternaria kikuchiana*
A.m.; *Alternaria mali*
G.c.; *Glomerella cingulata*

What is claimed is:

1. An azole-substituted cycloalkanol derivative represented by the formula (I):

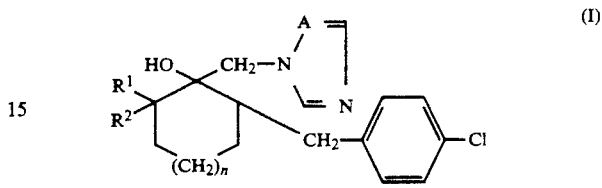

wherein $R^1$ represents a lower alkyl group, $R^2$ represents a hydrogen atom or a lower alkyl group, n is an integer of 1 or 2 and A represents a CH group.

2. The azole-substituted cycloalkanol derivative according to claim 1, wherein said lower alkyl group is an alkyl group having 1 or 2 carbon atoms.

3. An agriculturally and horticulturally fungicidal composition, which comprises an effective amount of an azole-substituted cycloalkanol derivative, as an active ingredient, represented by the formula (I):

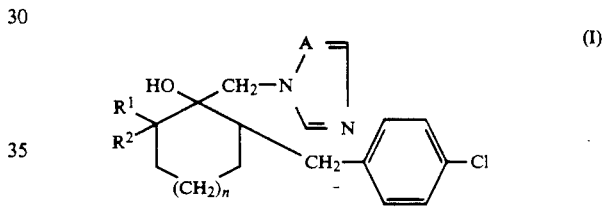

wherein $R^1$ represents a lower alkyl group, $R^2$ represents a hydrogen atom or a lower alkyl group, n is an integer of 1 or 2 and A represents a nitrogen atom or a CH group, and a suitable carrier or diluent.

4. The agriculturally and horticulturally fungicidal composition according to claim 3, wherein said lower alkyl group is an alkyl group having 1 or 2 carbon atoms.

* * * * *